US00PP32998P3

(12) United States Plant Patent
Beckman

(10) Patent No.: US PP32,998 P3
(45) Date of Patent: Apr. 20, 2021

(54) CALLA LILY PLANT NAMED 'ROYAL PLUM'

(50) Latin Name: *Zantedeschia sprengeri*
Varietal Denomination: Royal Plum

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,422

(22) Filed: Oct. 1, 2019

(65) Prior Publication Data

US 2020/0113106 P1 Apr. 9, 2020

Related U.S. Application Data

(60) Provisional application No. 62/766,205, filed on Oct. 4, 2018.

(51) Int. Cl.

*A01H 6/10* (2018.01)
*A01H 5/02* (2018.01)
*A01H 6/56* (2018.01)

(52) U.S. Cl.

USPC ..... Plt./490
CPC ..... *A01H 6/56* (2018.05)

(58) Field of Classification Search

USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Royal Plum' is a new variety of calla lily plant having red-purple colored spathes. The flower stems are strong and long lasting. The leaves are green with maculations present.

1 Drawing Sheet

Botanical classification: *Zantedeschia sprengeri*.
Varietal denomination: 'Royal Plum'.

BACKGROUND OF THE NEW PLANT

The present invention comprises a new and distinct cultivar of calla lily, botanically known as *Zantedeschia sprengeri* and hereinafter referred to by the cultivar name 'Royal Plum'.

'Royal Plum' is a product of a planned breeding program having the objective of creating *Zantedeschia* varieties for pot flower production in a wide range of colors and classic flower shapes. 'Royal Plum' was selected in 2010 in Moss Landing, Calif. as an inbred seedling selected from an open-pollinated population and self-pollinated for many generations. As such, its exact parentage is unknown and comparisons thereto cannot be provided.

The new variety was first asexually reproduced through tissue culture shoot propagation in October of 2011 in Moss Landing, Calif. Asexual reproductions of 'Royal Plum' have demonstrated that the combination of characteristics as herein disclosed for the new variety are retained and reproduced true to type through successive generations of asexual reproduction.

The following observations, measurements and comparisons describe plants grown in 15 cm pots at 77 days from planting in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Royal Plum' which, in combination, distinguish this calla lily as a new and distinct cultivar:

1. Red-purple colored spathes;
2. Strong peduncles; and
3. Leaf maculations present.

Table 1 provides a comparison of 'Royal Plum' to similar *Zantedeschia sprengeri* varieties 'Twilight' (unpatented) and 'California Red' (unpatented). Further, the plant and spathes are taller than those of 'Twilight'.

TABLE 1

| Comparison variety | Differing trait(s) | Comparison expression | Present variety expression |
|---|---|---|---|
| 'Twilight' | Spathe color | Lavender | Red-Purple Group RHS 61A to 61B (upper surface) and 71B to 71C (lower surface) |
| | Peduncle strength | 14 days to nodding | 28 days to nodding |
| 'California Red' | Leaf maculations | None present | Present |

BRIEF DESCRIPTION OF THE DRAWING

The accompanying photographic drawing illustrates the new variety at 77 days from planting, with the colors being as nearly true as is possible with color illustrations of this type.

DESCRIPTION OF THE NEW PLANT

Type: Deciduous.
Form: Semi-spreading.

Average spread: 28-33 cm.
Branch number: Average.
Branch color: Yellow-Green Group RHS 144B to 144C.
Height of leaf canopy above the soil: 7-10 cm.
Height of top of inflorescences above the soil: 21-28 cm.
Number of inflorescences per tuber: 16-18 cm in diameter: 8-12.
Lastingness of inflorescences on the plant: About 14 days.
Main use: Potted plant and cut flower.
Average time of flowering: Tubers planted in the field in May in 't Zand, The Netherlands bloom in July. Tubers planted in a greenhouse in February in 't Zand, The Netherlands bloom in April.
Disease/pest resistance: Strong tolerance to *Pythium* root rot and *Erwinia* bulb soft rot.
Hardiness: Not tested.
Leaves:
*Number per plant.*—12-20.
*Width.*—6.5-8 cm, with broadest position in the middle.
*Length.*—17-21 cm.
*Shape.*—Lanceolate.
*Apex.*—Apiculate.
*Base.*—Attenuate.
*Margin.*—Entire.
*Color.*—Upper surface: Yellow-Green Group RHS 147A, with Greyed-Green Group RHS 195C to 195D maculations present. Lower surface: Yellow-Green Group RHS 147B, with Greyed-Green Group RHS 196C to 196D maculations present.
*Surface texture.*—Smooth (both surfaces).
*Leaf venation.*—Pattern: Pinnate. Color: Yellow-Green Group RHS 147B to 147C.
*Lobes.*—None present.
*Petiole.*—Length: 7-10 cm. Diameter: 10-15 mm. Texture: Smooth. Shape: Cylindrical. Strength: Strong. Color: Upper surface: Green Group RHS 137A to 137B. Lower surface: Green Group RHS 138A to 138B.
Spathe:
*Length.*—5-7 cm.
*Width.*—3.5-5 cm.
*Fragrance.*—None.
*Shape.*—Cupped.
*Texture.*—Smooth.
*Apex.*—Apiculate.
*Base.*—Amplexicaul.
*Margin.*—Entire.
*Color.*—Throat spot: Red-Purple Group RHS 72A. Upper surface: Red-Purple Group RHS 61A to 61B. Lower surface: Red-Purple Group RHS 71B to 71C.
Spadix:
*Length.*—20-30 mm.
*Diameter.*—6-10 mm.
*Color.*—Yellow Group RHS 12B to 12C.
*Position relative to spathe.*—Upright from base.
*Apex.*—Rounded and Yellow Group RHS 12B to 12C.
*Pollen amount.*—Abundant.
Peduncle:
*Strength.*—Strong and erect, with no nodding observed until day 28.
*Length.*—20-27 cm.
*Diameter.*—10-12 mm.
*Texture.*—Smooth.
*Color.*—Base: Yellow-Green Group RHS 144B to 144C. Upper portion: Green Group RHS 143A.
Seeds:
*Number/flower.*—8.
*Length.*—2.6-4.2 mm.
*Diameter.*—1.9-2.8 mm.
*Color.*—White Group RHS 155C.
Reproductive organs:
*Anther.*—Shape: Round. Length: Less than 1 mm. Color: Yellow Group RHS 8B to 8C.
*Filament.*—Length: Less than 1 mm. Color: White Group RHS 155D.
*Style.*—Length: Less than 1 mm. Color: Yellow Group RHS 8B to 8C.
*Pistil.*—Number: 15-30. Length: About 1 mm.
*Stigma.*—Shape: Round. Length: Less than 1 mm. Diameter: Less than 1 mm.
*Ovaries.*—Texture: Smooth. Length: Varies between 1 to 10 mm. Diameter: Varies between 1 to 10 mm. Color: Top: Green Group RHS 142B to 142C. Bottom: Greyed-Red Group RHS 181B to 181C.

I claim:

1. A new and distinct variety of calla lily plant named 'Royal Plum' as herein described and illustrated.

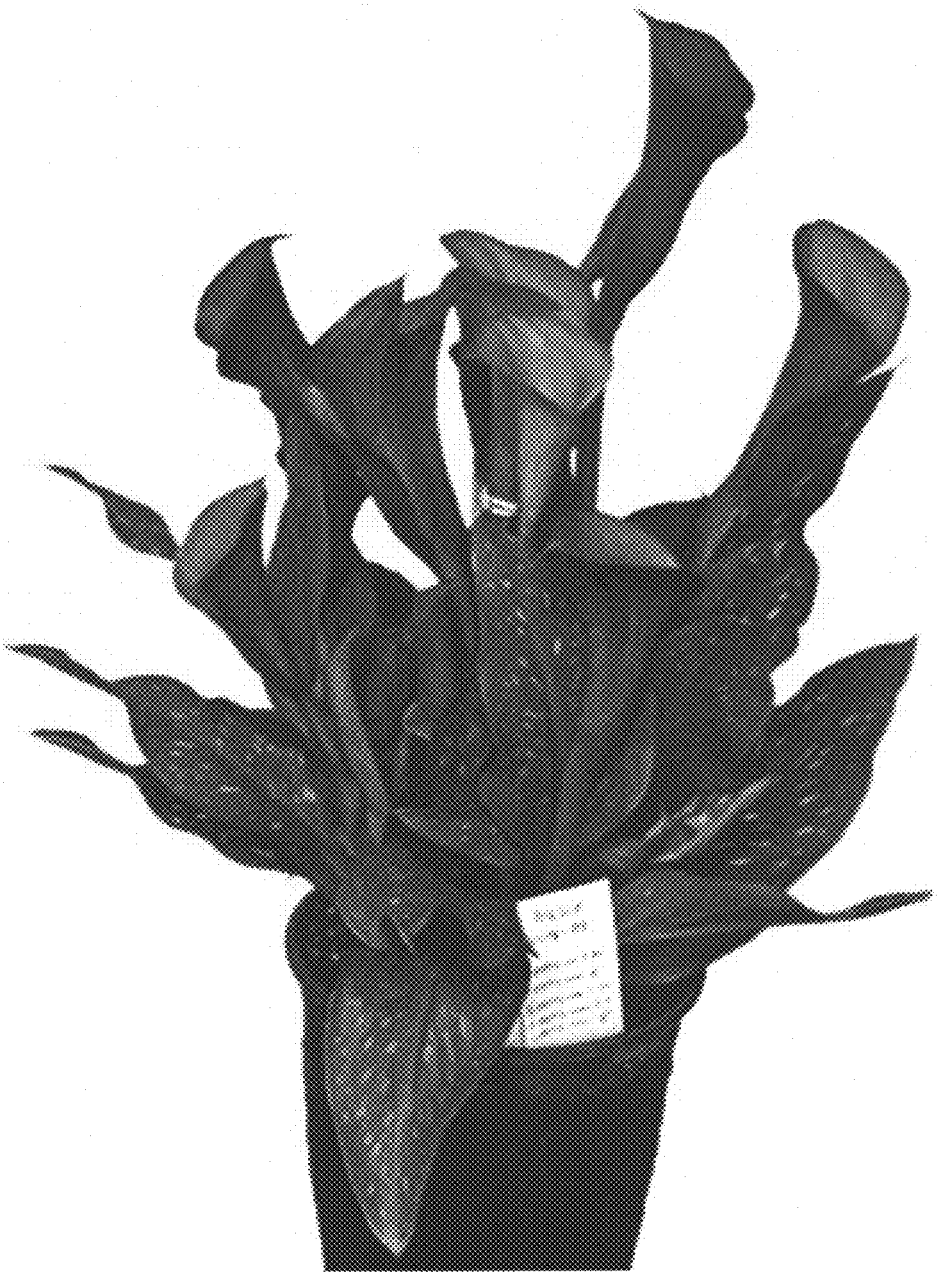

* * * * *